Figure 4:
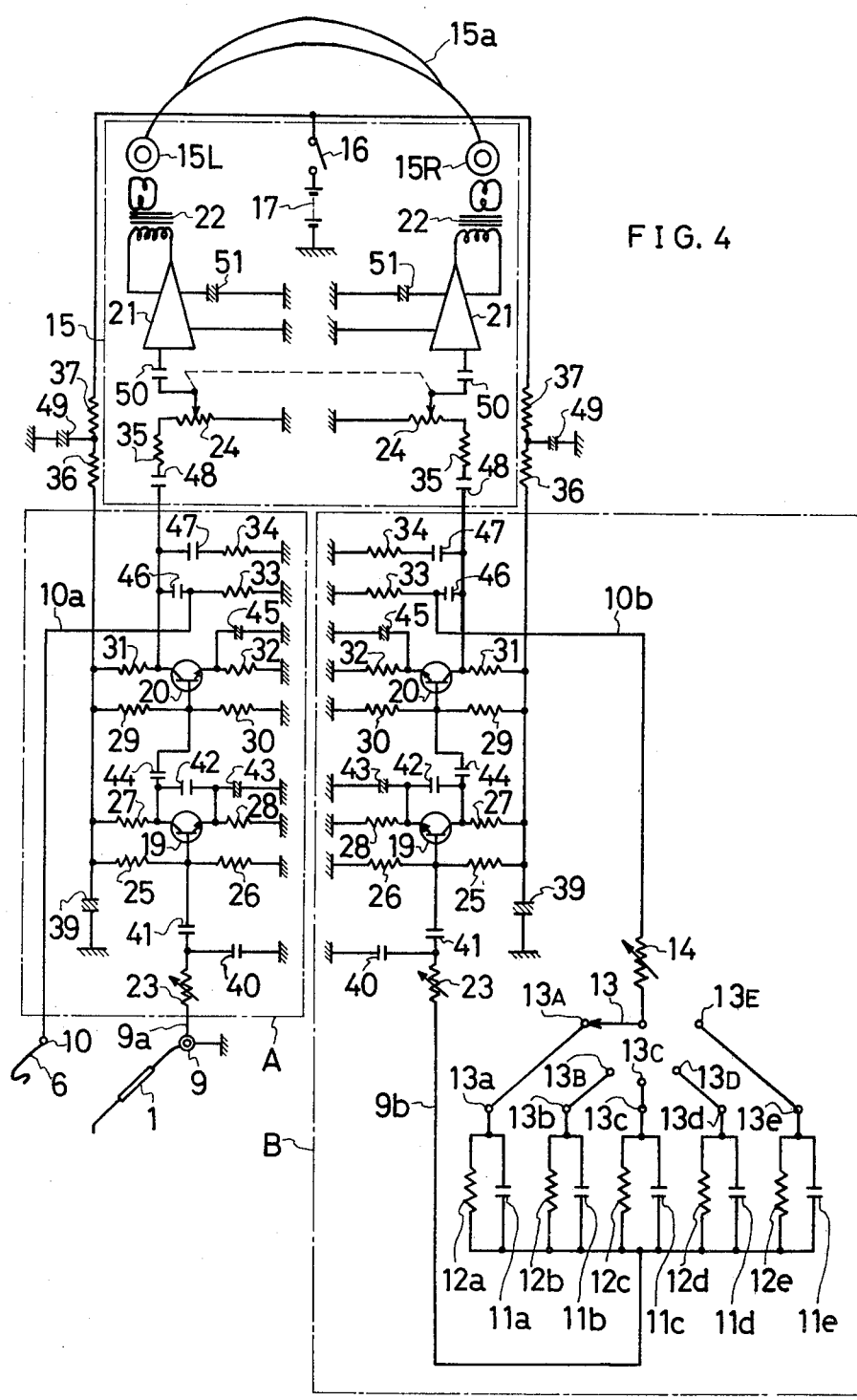

United States Patent [19]

Inoue

[11] 4,302,627
[45] Nov. 24, 1981

[54] DENTAL STETHOSCOPE

[75] Inventor: Noboru Inoue, Tokyo, Japan

[73] Assignee: Kabushiki Kaisha Dental Electronics Kenkyujo, Tokyo, Japan

[21] Appl. No.: 144,487

[22] Filed: Apr. 28, 1980

[30] Foreign Application Priority Data

Aug. 9, 1979 [JP] Japan ................................ 54-101430

[51] Int. Cl.³ ............................................. A61C 19/04
[52] U.S. Cl. .................................. 179/1 ST; 128/734
[58] Field of Search ............. 179/1 ST; 128/734, 741, 128/774, 776

Primary Examiner—George G. Stellar
Attorney, Agent, or Firm—Cullen, Sloman, Cantor, Grauer, Scott & Rutherford

[57] ABSTRACT

A measurement channel oscillator and a reference channel oscillator are provided in combination, a measurement probe and a mouth mucose lead element are respectively connected to the measurement channel oscillator, while one of a plurality of equivalent circuits each consisting of a pair of equivalent capacitor and equivalent resistor connected in parallel is selectively connected to the reference channel oscillator, the respective equivalent circuits corresponding to different stages of a decayed tooth, and the outputs of the measurement channel oscillator and the reference channel oscillator are respectively connected through the respective channels of a 2-channel stereo amplifier to a stereo head-phone, whereby an erosion stage of a decayed tooth can be correctly examined even if it is located at a hardly visible position in the mouth.

2 Claims, 6 Drawing Figures

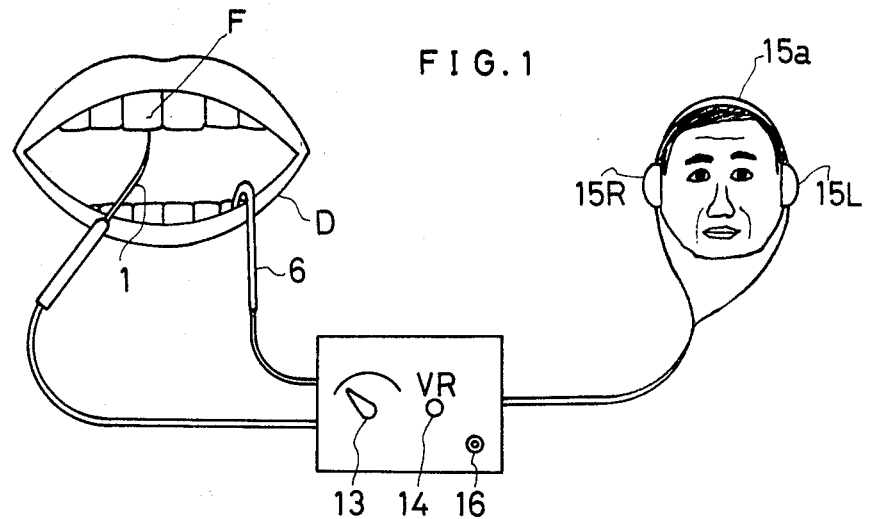
FIG. 1
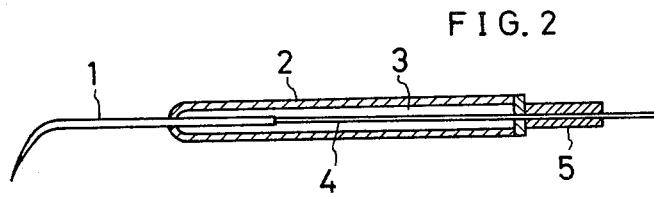
FIG. 2
FIG. 3
FIG. 6
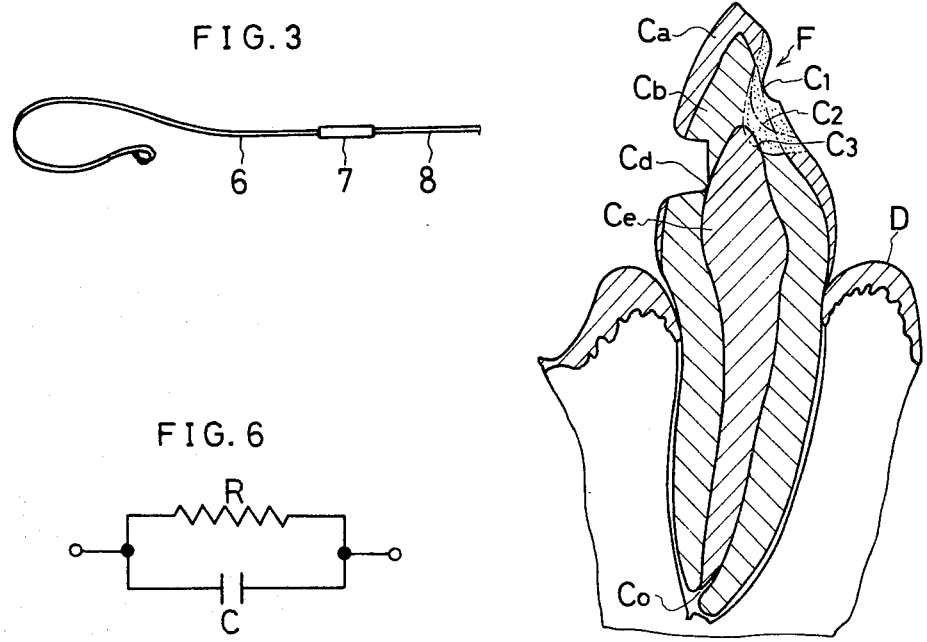
FIG. 5

DENTAL STETHOSCOPE

The present invention relates to a dental stethoscope for dental examination of a diseased part of a tooth such as decayed teeth or the like.

Recently, in accordance with the progress in the electronics, many medical diagnostic methods have been developed and thereby it has become possible to make an accurate diagnosis. However, the role of the stethoscope in medical diagnosis is still very large, and so, a doctor cannot do without the stethoscope even for a while. This is because the stethoscopy depends upon the sense of hearing that is most sensitive among the five senses of the human being, and hence a considerably accurate diagnosis can be made thereby as compared to the other methods, and because the use of the stethoscope is simple. However, for the disease of the hard tissues of the teeth, the stethoscopy has not been tried at all, although the visual examination, percussion, palpation, rocking test, X-ray diagnosis, examination by penetrating rays, electric diagnosis were effected in the past.

This will be due to the fact that the examination must be effected for an object consisting of special organs surrounded by hard tissues such as enamel, a dentine, etc. which are different from other tissues and generally called "teeth hard tissues". Heretofore, in order to confirm the degree of erosion of a decayed tooth in the past, the portion of the tooth in question must be ground away to know the degree. Even in such cases, skill was required to avoid a wrong diagnosis. Moreover, in the case of a tooth located at a hardly visible position in the mouth, the examination was especially difficult, and hence there was a fear that one may make a wrong diagnosis and that despite of a lightly decayed tooth, inadvertently the tooth may be ground away up to the portion of the nerve upon treatment. In addition, although the diagnostic method has been heretofore known in which the degree of erosion of a decayed tooth was perceived by measuring a resistance value between the diseased portion and the mucose of the mouth by means of a tester or the like, it was quite difficult for a dentist to look at the pointer of the tester and read the scale because he was always watching the decayed tooth and treating it with his both hands.

Therefore, it is one object of the present invention to provide a dental stethoscope which enables a dentist to make a dental diagnosis in a simple manner merely relying upon the sense of hearing, without visually inspecting the stage of the decayed tooth, without determining the stage by really grinding the decayed tooth, without watching a pointer of a tester, and without using X-rays or the like.

Another object of the present invention is to provide a dental stethoscope which enables a dentist to correctly examine a decayed tooth without leading to a wrong diagnosis even if the decayed tooth is located at a hardly visible position in the mouth.

According to one feature of the present invention, there is provided a dental stethoscope, in which a measurement channel oscillator and a reference channel oscillator are provided in combination, a measurement probe and a mouth mucose lead element are respectively connected to said measurement channel oscillator, while one of a plurality of equivalent circuits each consisting of an equivalent capacitor and an equivalent resistor connected in parallel to each other is selectively connected to said reference channel oscillator, the respective equivalent circuits corresponding to different stages of a decayed tooth, and the outputs of said measurement channel oscillator and said reference channel oscillator are respectively connected through the respective channels of a 2-channel stereo amplifier to a stereo head-phone.

The above-mentioned and other features and objects of the present invention will become more apparent by reference to the following description of its preferred embodiment taken in conjunction with the accompanying drawings, wherein:

FIG. 1 is a front view showing the condition of use of a dental stethoscope according to the present invention, FIG. 2 is an enlarged cross-section view of a measurement probe portion in the dental stethoscope shown in FIG. 1, FIG. 3 is an enlarged view of a mouth mucose lead element portion of the dental stethoscope shown in FIG. 1, FIG. 4 is an electric circuit diagram of the dental stethoscope shown in FIG. 1, FIG. 5 is an enlarged cross-section view of a tooth having a diseased portion, and FIG. 6 is an equivalent circuit diagram for the tooth having a diseased portion as shown in FIG. 5.

Referring now to FIGS. 1 and 4 of the drawings, in the illustrated dental stethoscope, a measurement channel CR-oscillator A and a reference channel CR-oscillator B are provided in combination, a measurement probe 1 and a mouth mucose lead element 6 are respectively connected to the measurement channel CR-oscillator A, while a plurality of equivalent circuits each consisting of an equivalent resistor 12a–12e and an equivalent resistor 11a–11e connected in parallel to each other is selectively connected via a switch 13 to the reference channel CR-oscillator B, the respective equivalent circuits corresponding to different stages of a decayed tooth, and the outputs of the measurement channel CR-oscillator A and the reference channel CR-oscillator B are respectively connected via the respective channels of a 2-channel stereo amplifier 15 to the respective receivers 15L and 15R of a stereo head-phone 15a.

In this dental stethoscope, details of the measurement channel CR-oscillator A are illustrated within a chain line frame A in the lower left portion of FIG. 4, in which transistors 19 and 20 are cascaded, between the collector of the output side transistor 20 and the ground are serially connected a capacitor 46 and a resistor 33 in sequence, the junction point in the series connection is connected via a feedback line 10a to a terminal 10 to be connected to the mouth mucose lead element 6, one end of a variable resistor 23 is connected via a lead 9a to a terminal 9 to be connected to the measurement probe 1, and the other end of the variable resistor 23 is connected via a capacitor 41 to the base of the transistor 19 and is also connected via a capacitor 40 to the ground. The base of the transistor 19 is grounded through a resistor 26 and is also connected via a resistor 25 to a high voltage side resistor 36. The emitter of the transistor 19 is grounded through a resistor 28, while the collector of the same transistor 19 is connected via a resistor 27 to the high voltage side resistor 36, and the junction point between the resistors 25 and 36 is grounded via the capacitor 39. The base of the transistor 20 is grounded through a resistor 30, and is also connected via a resistor 29 to the high voltage side resistor 36. In addition, the emitter of the transistor 20 is grounded via a resistor 32, while the collector of the transistor 20 is connected via a resistor 31 to the high voltage side resistor 36. Furthermore, between the collector and emitter of the transistor 19 is connected a by-pass capacitor 42, the emitter being grounded via a capacitor 43, and the collector of the transistor 19 is connected through a coupling capacitor 44 to the base of the transistor 20. One end of a series circuit consisting of a capacitor 47 and a resistor 34 is connected to the collector of the transistor 20, and the other end of the series circuit is grounded. Also the emitter of the transistor 20 is grounded via a capacitor 45.

Details of the reference channel CR-oscillator B are illustrated within a chain line frame B in the lower-right portion of FIG. 4, in which component parts having the same functions as those included in the above-described measurement channel RC-oscillator A are given like reference numerals. The structural difference of the reference channel CR-oscillator B from the measurement channel CR-oscillator A exists in the following points. That is, the junction point between the capacitor 46 and the resistor 33 is connected through a feedback line 10b to one end of a variable resistor 14 instead of the terminal 10 to be connected to the mouth mucose lead element 6, one ends 13a to 13e of a plurality of equivalent circuits each consisting of a corresponding one of equivalent resistors 12a to 12e and a corresponding one of equivalent capacitors 11a to 11e connected in parallel to each other, are connected respectively to stationary contacts 13A to 13E of a rotary switch 13 so that one of the equivalent circuits can be selectively connected to the variable resistor 14 by appropriately positioning a movable contact (represented by an arrowed line segment) of the rotary switch 13, and the other ends of the respective equivalent circuits are connected in common and also to a variable resistor 23 via a lead 9b.

Although not shown in FIG. 4, in the proximities of the respective stationary contacts 13A, 13B, 13C, 13D and 13E of the rotary switch 13 are indicated characters or symbols representing different stages $C_1, C_2, \ldots, C_n$ of erosion of a decayed tooth as will be described later with reference to FIG. 5.

In the subsequent portion of the stethoscope circuit, a series connection of a capacitor 48, resistor 35 and a potentiometer 24 having its free end grounded is connected to the collector of the transistor 20 in the measurement channel CR-oscillator A. The movable contact of the potentiometer 24 is coupled via a capacitor 50 to one of IC type amplifiers 21 in a 2-channel stereo amplifier 15, and the output of the IC type amplifier 21 is connected via a transformer 22 to a stereo head-phone 15a. A D.C. power supply 17 is connected through a power switch 16 to one end of the series connection of resistors 37 and 36 in that sequence, the junction point between these resistors 37 and 36 is grounded via a capacitor 49, and the other end of the series connection is connected to the ungrounded end of the above-described capacitor 39. A desired terminal of the IC type amplifier 21 is grounded via a capacitor 51. The above-described circuit construction in the 2-channel stereo amplifier 15 is also true for the other channel of the stereo amplifier 15 to be connected to the reference channel CR-oscillator B.

In a measurement probe assembly illustrated in FIG. 2, a measurement probe 1 having a predetermined length and a predetermined configuration is insulatively fixed to a tip end portion of a holder 2 made of a metallic cylinder, to the inner end of the measurement probe 1 is connected one end of a lead wire 4 inserted into a hollow space 3 in the holder 2, and the other end of the lead wire 4 is connected via a shield wire 5 extending from the rear end of the holder 2 to the terminal 9 of the measurement channel CR-oscillator A in FIG. 4.

A mouth mucose lead element 6 made of a metallic strip as shown in FIG. 3 is connected via a holder 7 to a lead wire 8 which is connected to the terminal 10 of the measurement channel CR-oscillator A in FIG. 4.

Referring now to FIG. 5 which shows a cross-section of a decayed tooth, reference character $C_a$ designates an enamel of the tooth, character $C_b$ designates a dentine, character $C_d$ designates an exposed dental pulp which appears in an misground hole of the tooth, character $C_e$ designates the dental pulp, and character $C_o$ designates a hole at a tip end of a tooth root.

In addition, reference characters $C_1$, $C_2$ and $C_3$ designate varieties of a decayed tooth according to the different stages of erosion of the decayed tooth at a diseased portion F of the tooth, $C_1$ representing the stage where only the enamel $C_a$ is eroded, $C_2$ representing the stage where the erosion proceeded up to the dentine $C_b$, and $C_3$ representing the stage where the erosion proceeded up to the interior of the dental pulp $C_e$. Such a diseased portion of a tooth is deemed to be equivalent to a parallel connection of a resistor and a capacitor. In FIG. 6, a resistor R represents the equivalent resistor of the diseased portion of the tooth, and a capacitor C represents the equivalent capacitor of the same portion.

Upon making a diagnosis by making use of the dental stethoscope according to the present invention, the mouth mucose lead element 6 is brought into contact with the mouth mucose D, and also the measurement probe 1 is made to contact with the diseased portion F of the tooth. Then a series circuit consisting of the feedback line 10a, terminal 10, mouth mucose lead element 6, diseased portion F of the tooth, measurement probe 1, terminal 9, lead line 9a and variable resistor 23 is completed from the junction point between the capacitor 46 and the resistor 33 in the measurement channel CR-oscillator A, so that a positive feedback is applied from the output side of the transistor 20 to the input side of the transistor 19 in the measurement channel CR-oscillator A. Consequently, the measurement channel CR-oscillator oscillates at a frequency corresponding to the respective stage of erosion at the diseased portion of the decayed tooth.

On the other hand, in the reference channel CR-oscillator B, a positive feedback is applied from the output side of the transistor 20 to the input side of the transistor 19 through a series circuit extending from the junction between the capacitor 46 and the resistor 33 and consisting of the feedback line 10b, variable resistor 14, rotary switch 13, one of the parallel connection circuits including the corresponding pairs of the equivalent resistors 12a to 12e and the equivalent capacitors 11a to 11e selected by the rotary switch 13, lead line 19b and variable resistor 23, and hence oscillation occurs in the feedback loop including the selected one of the equivalent circuits.

Then, the dentist listens to the oscillation tone from the measurement channel CR-oscillator A with one receiver of the head-phone 15a which is here assumed to be a left-side receiver 15L, while he is listening to the oscillation tone from the reference channel CR-oscillator B with the other receiver of the head-phone 15a which is here assumed to be a right-side receiver 15R.

As he is listening to the both oscillation tones, rotates the rotary switch 13 slowly to seek the position of the rotary switch 13 where the oscillation tone heard through the receiver 15R becomes nearly equal in pitch to the oscillation tone heard through the receiver 15L, and thus the various stages of a decayed tooth at the diseased portion of the tooth can be known by reading the index at the switch position. Alternatively, while an oscillation tone is generated from the reference channel CR-oscillator B with the rotary switch 13 preset at an arbitrary position on the contrary to the above-mentioned process, the measurement probe 1 is brought into contact with the diseased portion F of the tooth, then the oscillation tone which is issued intermittently from the measurement channel CR-oscillator A as the measurement probe 1 is put on and off the diseased portion F, is compared with the oscillation tone from the reference channel CR-oscillator B, and if there is any difference in pitch between the respective tones, the rotary switch 13 is rotated to another position and the respective tones are again compared with each other. The above operations are repeated until the pitches of the respective oscillation tones from the measurement channel CR-oscillator A and the reference channel CR-oscillator B becomes nearly equal to each other, when the index at the position of the rotary switch 13 is read and thus the stage of erosion of the decayed tooth is confirmed.

In the above-described measurement, if any difference in pitch still remains between the oscillation tone of the measurement channel CR-oscillator A heard through the receiver 15L and the oscillation tone of the reference channel CR-oscillator B heard through the receiver 15R, then the pitches of the tones heard through the left and right receivers 15L and 15R, respectively, can be almost equalized by finely adjusting the variable resistor 14. In this instance, by limiting the adjustable range of the variable resistor 14 to a predetermined scope, it can be prevented that the pitch of the oscillation tone in the adjustable range for one rotary switch position varies so widely that the variable range of the pitch overlaps with that for an adjacent rotary switch position.

According to the present invention, since the measurement channel CR-oscillator A and the reference channel CR-oscillator B are provided in combination, the measurement channel CR-oscillator A is brought into oscillation through a positive feedback circuit including the measurement probe 1 and the mouth mucose lead element 6, while the reference channel CR-oscillator is brought into oscillation through a positive feedback circuit including one of a plurality of equivalent circuits each consisting of an equivalent resistor and an equivalent capacitor which is selected by the rotary switch 13 in correspondence to different stages of erosion of a decayed tooth at the diseased portion F of the tooth, and the aforementioned respective CR-oscillators are connected via the respective channels of the 2-channel stereo amplifier 15 to the stereo head-phone 15a; the stage of erosion of a decayed tooth can be examined relying upon only the sense of hearing by equalizing the pitches of the respective oscillation tones heard through the respective receivers 15L and 15R of the stereo head-phone 15a while rotating the rotary switch 13. Moreover, since it is only necessary to bring the measurement probe 1 into contact with the diseased portion F of the decayed tooth, even a decayed tooth located at a hardly visible position can be reliably measured without necessitating a skill, and so, there is no fear of making a wrong diagnosis. Still further, as compared to the dental examination in the prior art in which the dentist is compelled to take an X-ray photograph, visually examine or examine through grinding, the X-ray hazards as well as pains caused by the grinding can be eliminated. In addition, the present invention mitigates the fatigue of the dentist caused by the need for visually finding out the changes occurring in the interior of a tiny tooth, obviates the mistake of inadvertently drilling up to the dental pulp in the case where it is intended to grind a tooth up to its dentine by grinding under an anesthetic condition, and enables the dentist to effect dental examination in an accurate and simple manner.

Besides the above-mentioned diagnosis, by making use of the fact that the pitch of the oscillation tone when the probe is brought into contact with the teethridge is identical to the pitch of the oscillation tone when the probe inserted into the root tube of the tooth reaches the hole at the tip of the tooth root and by utilizing the above-mentioned process for measurement, an accurate length of the tooth root tube can be perceived by measuring the depth of insertion of the probe 1 when the identical pitch of oscillation tone has been generated, without employing X-rays. Thus the present invention is very useful for diagnosis and treatment of teeth.

While the present invention has been described above in connection to its preferred embodiment illustrated in the accompanying drawings, the invention should not be limited only to the illustration in the drawings, but many changes and modifications of the illustrated embodiment could be made without departing from the scope of the present invention. For instance, in place of the combination of the plurality of equivalent resistors 12a to 12e, the plurality of capacitors 11a to 11e and the rotary switch 13 illustrated in FIG. 4, a single equivalent circuit consisting of a variable resistor and a variable capacitor connected in parallel could be used in the positive feedback loop of the reference channel CR-oscillator B.

What is claimed is:

1. A dental stethoscope characterized in that a measurement channel oscillator and a reference channel oscillator are provided in combination, a measurement probe and a mouth mucose lead element are respectively connected to said measurement channel oscillator, while at least one of equivalent circuits each consisting of an equivalent capacitor and an equivalent resistor connected in parallel to each other is selectively connected to said reference channel oscillator, said respective equivalent circuits corresponding to different stages of a decayed tooth, and the outputs of said measurement channel oscillator and said reference channel oscillator are respectively connected to the respective channels of a stereo head-phone.

2. A dental stethoscope as claimed in claim 1 characterized in that said measurement channel oscillator and said reference channel oscillator are CR-oscillators.

* * * * *